United States Patent [19]

Braun et al.

[11] Patent Number: 4,946,561
[45] Date of Patent: Aug. 7, 1990

[54] PROCESS FOR OBTAINING TRIOXANE FROM AQUEOUS SOLUTIONS BY HIGH-PRESSURE EXTRACTION

[75] Inventors: Gero Braun, Darmstadt; Karlheinz Burg; Karl-Friedrich Mück, both of Wiesbaden, all of Fed. Rep. of Germany

[73] Assignee: Hoechst Aktiengesellschaft, Fed. Rep. of Germany

[21] Appl. No.: 741,754

[22] Filed: Jun. 6, 1985

[30] Foreign Application Priority Data

Jun. 8, 1984 [DE] Fed. Rep. of Germany ....... 3421300

[51] Int. Cl.$^5$ .................... B01D 3/34; B01D 11/04; C07D 323/06
[52] U.S. Cl. ............................. 203/49; 203/14; 203/17; 203/50; 203/67; 203/70; 549/368
[58] Field of Search ................. 203/49, 71, 14, 17, 203/50, 67, 70; 549/368

[56] References Cited

U.S. PATENT DOCUMENTS

| 2,304,080 | 12/1942 | Frank | 549/368 |
| 2,347,447 | 4/1944 | Walker | 549/368 |
| 3,522,278 | 7/1970 | Montaubric et al. | 549/368 |
| 3,969,196 | 7/1976 | Zosel | 203/49 |
| 4,349,415 | 9/1982 | DeFilippi et al. | 203/49 |
| 4,437,938 | 3/1984 | Bhise et al. | 203/49 |

FOREIGN PATENT DOCUMENTS

| 1543815 | 9/1973 | Fed. Rep. of Germany . |
| 186975 | 10/1984 | Japan | 549/368 |
| 1012372 | 12/1965 | United Kingdom . |

Primary Examiner—Wilson Bascomb
Attorney, Agent, or Firm—Connolly and Hutz

[57] ABSTRACT

The invention relates to a process for obtaining trioxane from aqueous solutions by high-pressure extraction using an extracting agent which is in the form either of a gas in the supercritical state or of a liquid gas. An intermediate separation is advantageous, especially in the former case.

The trioxane can be obtained in high concentration and with a saving of energy by the process according to the invention.

18 Claims, 1 Drawing Sheet

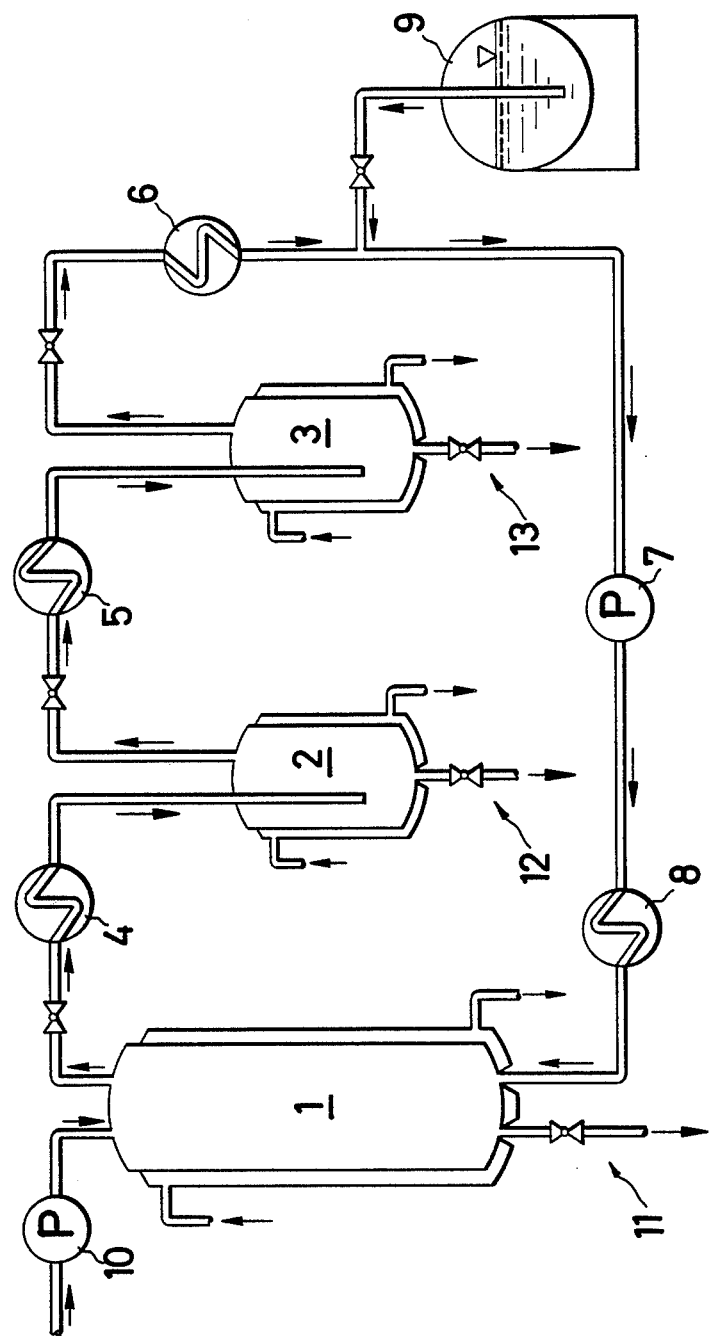

PROCESS FOR OBTAINING TRIOXANE FROM AQUEOUS SOLUTIONS BY HIGH-PRESSURE EXTRACTION

In the present state of the art, trioxane is usually prepared by heating 30–70% strength aqueous formaldehyde solutions in the presence of acid catalysts, for example 2 to 25% strength mineral acid (German Patent No. 1,543,390), or in the presence of acid ion exchangers (German Patent No. 1,135,491). In these processes, the trioxane is removed from the reaction mixture by distillation. This is carried out either in a column placed on the reactor, in accordance with U.S. Pat. No. 2,304,080, or in a separate column, as described in British Patent No. 1,012,372. The distillate rich in trioxane is extracted with, for example, methylene chloride or benzene, and neutralization and then purification by distillation are carried out as described in, for example, German Auslegeschrift No. 1,543,815.

It is common to the known processes for the removal of trioxane from the reaction mixture or from the distillate from the reactor that they are troublesome and energy-intensive. Furthermore, large amounts of extracting agents are necessary, and these may pollute the environment and be objectionable from the viewpoint of health.

Thus, the object according to the invention was to make available an efficient material separation process which is less energy-intensive and less environmentally polluting and with which it is possible to remove from the aqueous reaction solution, after completion of or during the reaction, the trioxane which has been produced.

To achieve this object, the invention proposes a process for the isolation from an aqueous solution of the trioxane which has been produced, by treatment of this solution with an extracting agent which is a gas in the supercritical state or a liquefied gas (liquid gas).

Thus the present invention relates to a process for the isolation of trioxane from dilute aqueous solutions, containing formaldehyde, by treatment with an extracting agent, which comprises the extracting agent being a gas in the supercritical state or a liquid gas.

The high-pressure extraction of organic substances from, inter alia, aqueous solutions using supercritical media has in fact already been disclosed. Thus, for example, U.S. Pat. No. 4,250,331 describes this procedure for the extraction of organic acids from dilute aqueous solutions of the corresponding salts. The extraction temperatures mentioned are 35°–200° C. In spite of the extraction temperatures sometimes being high, and the amounts of water which are carried over during this being large, the separation out of the dissolved substances is carried out in only one stage by reducing the pressure. No attempt is made to separate out an extract which contains as little water as possible. In addition, the degrees of extraction achieved are only 1–23%.

In one of the two embodiments according to the invention, the extracting agent should be in the supercritical state. To attain this, the temperature and the pressure under which this process variant according to the invention is carried out must be at least the critical temperature and critical pressure respectively of the particular extracting agent, but are preferably above them. In general, temperatures between the critical temperature and 200° C., preferably 120° C., are possible. The temperatures are particularly preferably between 5° C. and 70° C. above the critical temperature. The corresponding pressures are between the critical pressure and 1,000 bar, preferably 400 bar, and in particular between 30 bar and 300 bar, above the critical pressure. It is advantageous in this process to use an appropriate extracting agent under an extraction pressure such that the solubility in the supercritical gas of the trioxane which is to be extracted depends as little as possible on the temperature. In this way, the separation out of major amounts of trioxane in the intermediate separation, which is preferably carried out according to the invention, is avoided.

The extracting agents which can be used according to the invention are the compounds known for high-pressure extraction, where appropriate as mixtures, as long as they are inert towards trioxane. Examples which may be mentioned here are: aliphatic hydrocarbons having, for example, 1 to 6 carbon atoms, and halogen-containing hydrocarbons, such as trifluoromethane, chlorodifluoromethane, chlorotrifluoromethane, dichlorodifluoromethane or bromotrifluoromethane. It is also possible to use for this purpose inorganic gases, such as carbon dioxide, sulfur dioxide, ammonia, sulfur hexafluoride or dinitrogen oxide. Where appropriate, it is also possible to use media acting as so-called entrainers, such as methanol, ethanol, dimethylformamide, acetone, acetonitrile, benzene, toluene and the like.

Preferred extracting agents are relatively nonpolar gases, such as carbon dioxide.

According to the other, less preferred, embodiment according to the invention, the extracting agent is in the subcritical state and, under the extraction conditions, is in the form of a liquid gas. The temperature in this case is generally between 0° C. and the critical temperature, preferably in the region of 0° C. and 5° C. below the critical temperature. The corresponding pressures advantageously vary between 5 bar and 500 bar, preferably between 10 bar and 150 bar above the particular vapor pressure of the liquid gas.

The aqueous trioxane solution which is to be extracted according to the invention may be the reaction solution as is produced after completion of the reaction of formaldehyde to give trioxane. However, according to the invention it is also possible for the solution which is being formed during the reaction to be treated directly with the extracting agent. The trioxane concentration in this trioxane solution can vary within wide limits. The concentration is normally in the range up to 10% by weight, preferably 3 to 7% by weight, in each case relative to the total solution. In addition, solutions of this type still contain considerable amounts of formaldehyde and the acid catalyst (mineral acid, acid ion exchanger and the like). As a rule, they also contain as by-products methanol, formic acid, methyl formate, methylal, dioxymethylene dimethyl ether, dioxane, trioxepane, dimethylbicyclotetroxane, methylbicyclotetroxane, bicyclotetroxane, tetroxane etc.

The process according to the invention is carried out in a manner known per se, the extracting agent, whether in the supercritical state or as a liquid gas, being preferably recycled. It is possible for the procedure for this to be both discontinuous and continuous. The latter can be carried out by, for example, countercurrent extraction of the trioxane solution in a highpressure extraction column (for example a sieve plate column).

The amount of the extracting agent is not critical and principally depends on the trioxane concentration and the extraction time. In general, it is 1 to 10 kg of extracting agent per kg of trioxane solution, preferably 2 to 4 kg/kg of trioxane solution.

It is also possible for the time during which the extracting agent is in contact with the aqueous trioxane solution to vary within wide limits, for example between 1 and 300 minutes, preferably between 5 and 60 minutes. The separation out of the substances dissolved in the extracting agent can be carried out in one or several stages, and is preferably carried out by reducing the pressure and/or by reducing or increasing the temperature. If, for example, the extracting agent is used in the supercritical state in accordance with the embodiment preferred according to the invention, the reduction in the pressure and/or the temperature can be carried out such that the pressure and temperature are still above the particular critical value, and thus the extracting agent remains in the supercritical state. In addition, it is also possible to decrease the temperature and pressure into the subcritical region and thus also to transfer the extracting agent into the subcritical region. The conditions which are preferably selected for this are such that the extracting agent remains in the form of a gas. Finally, in the separation out, it is possible for only the temperature or only the pressure to be reduced below the particular critical value. In this instance, the extracting agent remains in the form of a gas.

Since the loading of the extracting agent frequently decreases during the course of the extraction, and thus the dissolving power of the extracting agent is no longer completely utilized, when the loading has fallen below the maximum by, for example, 10%, the partially loaded extracting agent can also be passed additionally through a second extraction container filled with fresh trioxane solution.

It has proved advantageous, particularly in the case of high-pressure extraction of very dilute aqueous trioxane solutions at elevated temperatures and when supercritical gases are used as the extracting agent, to undertake an intermediate separation in order in this case to remove a large part of the water and formaldehyde which are carried over. This intermediate separation can be carried out in the manner described above for the single-stage separation. In most cases, this intermediate separation is carried out at a temperature which is between the extraction temperature and the critical temperature of the relevant fluid, preferably at 30° C. to 80° C., the pressure generally corresponding to the extraction pressure. However, it is preferable also for the pressure in the intermediate separator to be reduced below the extraction pressure, but the extracting agent preferably remains in the gaseous state during this. In the intermediate separator, a large part of the water which is carried over, usually more than 90% by weight, as well as up to 90% by weight of the formaldehyde which is carried over, is removed.

Then, by further reduction in the temperature and/or pressure in the final separator, as described above, a concentrated trioxane is obtained, and in most cases this is produced as a slurry of crystals.

In principle, it is also possible to use the intermediate separation when liquid gases are used as the extracting agents, but this variant is not preferred in this instance. On the contrary, in this case, the process is usually carried out in one stage, i.e. the loaded extracting agent is passed directly into a separator, since liquid gases usually dissolve only relatively little water, at least at low temperatures. The liquid gas is then evaporated in the separator, and there is accumulation of the dissolved organic substances. The re-liquefied gas is used again for further extraction. Surprisingly, it is possible in this way to obtain highly concentrated extracts even when the aqueous trioxane solutions are quite dilute. This particularly applies when the extraction temperature is not greatly above room temperature.

A preferred embodiment of the process according to the invention in the variant using a supercritical gas is described in detail below with reference to the FIGURE appended, The single FIGURE of drawing illustrates a process for the isolation of trioxane from aqueous solutions by extraction.

The extraction container (1), which is preferably constructed as a sieve plate column or multistage bubble column, and the intermediate (2) and final separator (3) are filled with the extracting agent from the tank (9). The extracting agent is compressed further to the extraction pressure in the container (1) which is maintained at the extraction temperature. Inside the extraction container, the extracting agent flows in the opposite direction to the aqueous trioxane solution, which possibly contains mineral acid as catalyst and which is metered in via the pump (10). During this, the supercritical medium is loaded with the trioxane and water to form a "supercritical condition". At (11), the less concentrated trioxane solution which has been treated with the extracting agent is drawn off. In contrast, the "supercritical solution" is transferred through the heat exchanger (4) into the intermediate separator (2) in which, at a pressure which is the same as or lower than that in the extraction container (1) and at a lower temperature, the major part of the water and of the formaldehyde is separated out and is discharged via (12). The remainder of the gas stream then passes through the heat exchanger (5) into the final separator (3) in which, by a reduction in the pressure, preferably to values below the critical pressure of the gas, the trioxane is separated out with a low moisture content and leaves the final separator via (13), where appropriate after previously being melted. The temperature during this can likewise be reduced to subcritical values, but it can also be left at the same level as in the intermediate separator (2) or even increased again. The gas stream from which the extract has been removed is passed from the container (3) through the heat exchanger (6) into the liquid gas pump or compressor (7), is compressed there and is transported through the heat exchanger (8) back to the extraction container (1). The recycling of the extracting agent is thus completed.

The water which has collected in the intermediate separator (2) is passed via (12) advantageously into a pressure-release vessel (not shown in the FIGURE) for degassing, and the gas is recovered as far as possible by pumping off and reliquefaction. A similar procedure is advisable when the separator (3) is opened. It is also possible to use a part of the gas for the partial filling with gas of a second separator (likewise not shown in the FIGURE) which is connected in parallel with the container (3).

Example 1

In an apparatus derived from that in the FIGURE, having an extraction container (2) (without immersion tube) and a separator (3), 557 g of a solution composed of 20.6% trioxane, 21.7% formaldehyde and 57.7% water were treated semicontinuously with 2.3 kg/h trifluoromethane for 5 h under a pressure of 150 bar and at a temperature of 80° C. Of the total of 214 g extracted, 190 g containing 46.6% trioxane and containing 13.2% formaldehyde were separated out in the container (3) under 40 bar and at 26° C. This corresponds to 77% of the total amount of trioxane in the solution employed. Taking into account the losses due to blowing off the trifluoromethane, and assuming complete separation out in (3), an extract containing 50.8% trioxane and containing 11.7% formaldehyde would be obtained, corresponding to a degree of extraction of trioxane (based on the starting solution) of 94.9%.

Example 2

In an apparatus as in Example 1, 555 g of a solution composed of 4.2% trioxane, 30% formaldehyde and 65.8% water were treated with 1.9 kg/h $CO_2$ for 6 h under a pressure of 150 bar and at a temperature of 80° C. Of the total of 31 g extracted, 21.7 g containing 41.9% trioxane and containing 13.3% formaldehyde were separated out under 50 bar and at 24° C. This corresponds to 39.3% of the total amount of trioxane in the solution employed. Taking into account the losses on blowing off, and assuming complete separation out, an extract containing 53.7% trioxane and containing 30.0% formaldehyde would be obtained, corresponding to a degree of extraction of trioxane of 72.1%.

Example 3

In an apparatus derived from that in the FIGURE, with a stirred autoclave as the extraction container (1) (stirring speed 500 min$^{-1}$) and with an intermediate separator (2) and a final separator (3), 542 g of a solution composed of 5% trioxane, 40% formaldehyde and 55% water were treated with 2 kg/h $CO_2$ for 2 h under a pressure of 200 bar and at a temperature of 100° C. Of the total of 73 g extracted, 42.5 g containing 6.2% trioxane and containing 33.6% formaldehyde were separated out in an intermediate separation under 70 bar and at 60° C. After a further reduction in the pressure and temperature to 50 bar and 26° C., 14.4 g containing 80.3% trioxane and containing 5.2% formaldehyde were separated out in container (3). Taking into account the losses on blowing off, and assuming complete separation out in (3), an extract containing 67.2% trioxane and containing 11.8% formaldehyde would be obtained, corresponding to a degree of extraction of trioxane of 75.7%. A total of 85.3% of the trioxane was extracted from the starting solution.

Example 4

In an apparatus derived from Example 3, without an intermediate separator (2), 3,500 g of a solution composed of 7% trioxane, 40% formaldehyde and 53% water were treated with 2 kg/h $CO_2$ for 7 hours under a pressure of 250 bar and at a temperature of 80°–85° C. Of the total of 360 g extracted, 338 g were obtained by a separation out at 45° C. and under 60 bar as an extract containing 56% trioxane and containing 16% formaldehyde. Taking into account the losses on blowing off, and assuming complete separation out in (3), an extract containing 60% trioxane and containing 15% formaldehyde would be obtained, corresponding to a degree of extraction of trioxane of 84%.

Example 5

In a sight autoclave of capacity 80 ml, 30 ml of a solution composed of 5% trioxane, 40% formaldehyde and 55% water were treated with 50 ml of liquid $CO_2$ while shaking for 2 h under a pressure of 100 bar and at a temperature of 19° C. After removal of the liquid $CO_2$ phase and evaporation of the $CO_2$, a yield of 0.9 g containing about 75% trioxane was obtained. Thus the degree of extraction was about 45%.

Example 6

In an apparatus as in Example 1, 600 g of a solution composed of 52.5% formaldehyde, 41.5% water and 6% sulfuric acid as catalyst were treated with 2 kg/h $CO_2$ for 6 h under a pressure of 200 bar and at a temperature of 100° C. During this, about 20.4 g of trioxane were formed, corresponding to a 6.5% conversion of formaldehyde. Of the total of 39 g extracted, 10 g containing 25.8% trioxane and containing 31.1% formaldehyde were separated out under 50 bar and at 24° C. Taking into account the losses on blowing off, and assuming complete separation out in (3), an extract containing about 19.9% trioxane and containing about 12.2% formaldehyde would be obtained, corresponding to a degree of extraction of the trioxane formed of about 40.8%.

We claim:

1. A process for the isolation of trioxane by treatment of a dilute aqueous reaction solution containing formaldehyde said solution being obtained (1) after completion of a reaction of formaldehyde to give trioxane, or (2) during said reaction of formaldehyde, the process comprising the steps of (a) contacting and thereby extracting the aqueous solution of trioxane with an extracting agent in an amount of 1–10 kg/kg of trioxane solution, said agent (a1) being maintained during the contacting under supercritical conditions in the temperature range between the critical temperature and 200° C. and in the pressure range between the critical pressure and 1000 bar of the extracting agent, thereby forming a supercritical solution or (a2) being in a subcritical state in the form of a liquified gas in the temperature range between the critical temperature of the liquified gas and 0° C. and a pressure between 5 bar and 500 bar above the particular vapor pressure of the liquified gas, thereby forming a subcritical solution, the resulting solutions of (a1) or (a2) comprising trioxane and extracting agent as well as water and formaldehyde which are coextracted, (b) separating the substances dissolved in the extracting agent in separators in one or several stages from the extracting agent by (b1) reducing the pressure or the temperature or both (b2) increasing the temperature, such that pressure and temperature are still above the above-mentioned particular critical values or by (b3) decreasing the temperature or the pressure or both into the subcritical region to separate the solutions obtained into the extracting agent and a mixture of concentrated trioxane which is in the form of a slurry of crystals, formaldehyde and water, which are separately discharged from the separators during the separation step.

2. A process as in claim 1 wherein in step (b) a large part of water and formaldehyde is separated intermediately from the solution by an intermediate separator, effecting said separation under a pressure corresponding to or lower than the extraction pressure and under a temperature between the extraction temperature and the critical temperature of the solution.

3. A process as in claim 1 wherein the supercritical conditions are in the temperature range between the critical temperature and 120° C. and in the pressure range between the critical pressure and 400 bar of the extracting agent.

4. A process as in claim 1 wherein the conditions in the subcritical state are in the temperature range of 0° C. and 5° C. below the critical temperature of the liquified gas and in a pressure range between 10 bar and 150 bar above the particular vapor pressure of the liquified gas.

5. A process as in claim 1 wherein the extracting agent is an aliphatic hydrocarbon having 1-6 carbon atoms, a halogenated hydrocarbon, sulfurhexafluoride, sulfurdioxide, dinitrogenoxide, carbondioxide or a mixture thereof.

6. A process as in claim 1 wherein the concentration of the trioxane solution to be extracted is up to 10% by weight relative to the total solution.

7. A process as in claim 1 wherein the amount of extraction agent is 2-4 kg/kg of trioxane solution.

8. A process as in claim 1 wherein the time during which the extracting agent is in contact with the aqueous trioxane solution is between 1 and 300 minutes.

9. A process as in claim 1 wherein the isolation of the trioxane is effected by a counter current high-pressure extraction.

10. A process as in claim 1 wherein the extracting agent is recovered after the discharge from the separators.

11. A process as in claim 1 wherein the extracting agent is recompressed.

12. A process as in claim 10 wherein the extracting agent is recycled into the contacting step (a).

13. A process as in claim 1 wherein the super-critical conditions are in the temperature range between 5° and 70° C. above the critical temperature and in the pressure range between 30 to 300 bar above the critical pressure of the extracting agent.

14. A process for the isolation of trioxane by treatment of a dilute aqueous reaction solution containing formaldehyde, said solution being obtained (1) after completion of a reaction of formaldehyde to give trioxane or (2) during said reaction of formaldehyde, the process comprising the steps of (A) contacting and thereby extracting the aqueous solution of trioxane with an extracting agent in an amount of 1-10 kg/kg of trioxane solution, said agent (A1) being maintained during the contacting under supercritical conditions in the temperature range between the critical temperature and 200° C. and in the pressure range between the critical pressure and 1000 bar of the extracting agent, thereby forming a supercritical solution or (A2) being in a subcritical state in the form of a liquified gas in the temperature range between the critical temperature of the liquified gas and 0° C. and a pressure between 5 bar and 500 bar above the particular vapor pressure of the liquified gas, thereby forming a subcritical solution, the solution comprising trioxane and extracting agent as well as water and formaldehyde which are coextracted, (B) separating a large part of water and formaldehyde intermediately from the solution by an intermediate separator, effecting said separation under a pressure corresponding to or lower than the extraction pressure and under a temperature between the extraction temperature and the critical temperature of the solution, (C) separating the substances dissolved in the extracting agent in one or several stages from the extracting agent by (C1) reducing the pressure or the temperature or both or (C2) increasing the temperature, such that pressure and temperatures are still above the above-mentioned particular critical values or by (C3) decreasing the temperature or the pressure or both into the subcritical region to separate the solutions obtained into the extracting agent and a mixture of concentrated trioxane which is in the form of a slurry of crystals, formaldehyde and water, which are discharged from the separator, and (D) recovering, recompressing and recycling stepwise the extracting agent into the contacting step (A).

15. A process as in claim 14 wherein the super-critical conditions are in the temperature range between 5° and 70° C. above the critical temperature and in the pressure range between 30 and 300 bar above the critical pressure of the extracting agent.

16. A process as in claim 14 wherein the concentration of the trioxane solution to be extracted is up to 10% by weight relative to the total solution.

17. A process as in claim 14 wherein the amount of extraction agent is 2-4 kg/kg of trioxane solution.

18. A process as in claim 14 wherein the conditions in the subcritical state are in the temperature range of 0° C. and 5° C. below the critical temperature of the liquified gas and in a pressure range between 10 and 150 bar above the particular vapor pressure of the liquified gas.

* * * * *